United States Patent [19]

Hoffmann et al.

[11] 4,148,824

[45] Apr. 10, 1979

[54] MANUFACTURE OF 1-DISUBSTITUTED AMINOALK-2-YN-4-OLS

[75] Inventors: Herwig Hoffmann, Frankenthal; Heinz Graefje, Ludwigshafen; Wolfgang Koernig, Dossenheim; Siegfried Winderl, Heidelberg-Wieblingen, all of Fed. Rep. of Germany

[73] Assignee: BASF Aktiengesellschaft, Fed. Rep. of Germany

[21] Appl. No.: 824,523

[22] Filed: Aug. 15, 1977

[30] Foreign Application Priority Data

Aug. 20, 1976 [DE]  Fed. Rep. of Germany ....... 2637425

[51] Int. Cl.² .............................................. C07C 85/02
[52] U.S. Cl. .............................. 260/585 B; 260/585 C
[58] Field of Search ......................... 260/585 B, 585 C

[56] References Cited

U.S. PATENT DOCUMENTS

| | | | |
|---|---|---|---|
| 3,448,153 | 6/1969 | Cavitt et al. | 260/585 B X |
| 3,520,932 | 7/1970 | Martin et al. | 260/585 C X |

*Primary Examiner*—Paul F. Shaver
*Attorney, Agent, or Firm*—Keil & Witherspoon

[57] ABSTRACT

The manufacture of N-disubstituted 1-aminoalk-2-yn-4-ols by reacting a secondary amine, e.g. a dialkylamine, formaldehyde and an acetylene-alcohol by a Mannich reaction, using a copper catalyst, takes place with better yield and at a higher rate if carried out in the presence of iodine or of a bromide or iodide.

7 Claims, No Drawings

MANUFACTURE OF 1-DISUBSTITUTED AMINOALK-2-YN-4-OLS

The manufacture of disubstituted aminoalk-2-yn-4-ols (N-disubstituted 1-amino-4-hydroxy-2-acetylenes), especially of the formula (I)

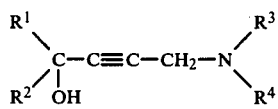

where $R^1$ is hydrogen or an aliphatic hydrocarbon radical and $R^2$ is hydrogen or an aliphatic or aromatic hydrocarbon radical, or $R^1$ and $R^2$ together with the carbon atom to which they are attached from a cycloaliphatic hydrocarbon radical, and $R^3$ and $R^4$ are each an aliphatic hydrocarbon radical, or $R^3$ and $R^4$ together with the nitrogen atom to which they are attached form a heterocyclic radical, by reacting secondary amines, formaldehyde and α-hydroxyacetylenes at an acid pH, generally from 3 to 6.8, in the presence of copper compounds is disclosed, for example, in German Pat. No. 1,100,617. In general, the reaction is classified under the Mannich condensation.

According to the above Patent, the yields obtained are from 75 to 82% of theory. The Patent further discloses that at least 5 parts of copper sulfate or copper acetate are required, per 100 parts of α-hydroxyacetylene, in order to achieve this result.

It is an object of the present invention to provide more active catalysts by means of which a higher yield of the desired product may be obtained. It is a further object of the invention to reduce the amount of catalyst required, since copper salts which may precipitate frequently cause operating problems.

We have found that the above objects are achieved and that N-disubstituted 1-aminoalk-2-yn-4-ols of the above formula I may be obtained in better yield, and with less catalyst, than hitherto, by reacting an alkynol with formaldehyde and a secondary amine in acid aqueous solution in the presence of a copper compound, if the reaction is carried out in the presence of a bromide or iodide which is soluble in the reaction mixture, or in the presence of iodine.

1-Dialkylaminoalk-2-yn-4-ols are valuable intermediates for the manufacture of crop protection agents and drugs.

The reaction of the amine, aqueous formaldehyde and α-hydroxyacetylene is generally carried out at a pH of from 2 to 7, preferably of about 5, and preferably in the presence of a mineral acid.

The bromides or iodides which are soluble in the reaction mixture may be, for example, the alkali metal salts of hydriodic acid or hydrobromic acid or, at least partly, the hydrohalic acids. Of course, they may also be used as a mixture. The copper compound employed is advantageously a chloride, nitrate or acetate, but preferably the sulfate, i.e. a Cu(II) compound soluble in the reaction mixture. The direct use of copper-I iodide appears to be less effective, possibly due to the fact that this compound is only sparingly soluble in the reaction mixture. This situation was not to be deduced from the known investigations in this field, e.g. the disclosures in German Laid-Open Application DOS No. 2,233,362 or in British Pat. No. 1,383,945; instead, it is evident that hitherto either Cu(I) compounds or Cu(II) compounds were added and a reaction of the catalyst itself was not considered.

The above radicals $R^1$ and $R^4$ may be hydrogen or aliphatic or aromatic hydrocarbon radicals having e.g. from 1 to 10 carbon atoms. The reaction in general does not depend on the nature of these radicals, unless they exhibit substituents which are known to the skilled worker to prevent or change the reaction under consideration.

Examples of compounds (I) that may be manufactured according to the invention are mono- and dimethylamino, mono- and diethylamino, methylbutylamino, methylisoprenylamino, phenylamino and decylamino derivatives of appropriate propynols, butynols, pentynols or decynols, the alkynols being straight-chain or branched.

The reaction may be carried out at a satisfactory rate at from about 65° C. to the boiling point of the mixture, preferably from 85° to 95° C. In principle, it is also possible to select a different temperature, given appropriate conditions.

The resulting salts of the dialkylaminoalkynols with mineral acids may be saponified with alkali or ammonia and worked up in the conventional manner. Experience shows the yield to be from 85 to more than 90% of theory.

In the Examples which follow, amounts are by weight, unless stated otherwise.

EXAMPLE 1

255 parts by weight of 55% strength aqueous but-3-yn-2-ol, 250 parts by weight of 30% strength aqueous formaldehyde, 161 parts by weight of diethylamine, 1.3 parts by weight of copper sulfate, 2 parts by weight of potassium iodide and 50 parts by weight of water are mixed with 115 parts by weight of concentrated sulfuric acid and the mixture is then brought to pH 4.5 with further sulfuric acid. It is then heated at 95° C. for 5 hours, cooled, mixed with 230 parts by weight of aqueous ammonia and extracted with 400 parts by weight of toluene. After distillation, 279 parts by weight of 1-diethylaminopent-2-yn-4-ol are obtained, corresponding to a yield of 90% of theory.

EXAMPLE 2

204 parts by weight of aqueous 55% strength propargyl alcohol, 250 parts by weight of 30% strength aqueous formaldehyde, 161 parts by weight of diethylamine, 1.4 parts by weight of copper sulfate, 2 parts by weight of potassium iodide, 50 parts by weight of water and 115 parts by weight of concentrated sulfuric acid are mixed and brought to pH 5. The mixture is heated for 5 hours at 92° C. and worked up as described. 242 parts by weight of 1-diethylaminobut-2-yn-4-ol are obtained, corresponding to a yield of 86%.

EXAMPLE 3

The procedure followed is as described in Example 1. Instead of 1.3 parts by weight, 2.3 parts by weight of copper sulfate are used, and instead of 2 parts by weight of potassium iodide, 2.3 parts by weight of potassium bromide are used. After working up, 270 parts by weight of 1-diethylaminopent-2-yn-4-ol are obtained, corresponding to a yield of 87.2%.

EXAMPLE 4

The procedure described in Example 2 is followed. Instead of 2 parts by weight of potassium iodide, 2 parts by weight of sodium iodide are employed. 244 parts by weight of 1-diethylaminobut-1-yn-4-ol are obtained, corresponding to a yield of 87%.

EXAMPLE 5

The procedure described in Example 1 is followed. Instead of 1.3 parts by weight, 2.3 parts by weight of copper sulfate are employed, and instead of 2 parts by weight of potassium iodide, 2.5 parts by weight of sodium bromide are employed. The reaction is carried out at 85° C. 268 parts by weight of 1-diethylaminopent-2-yn-4-ol are obtained, corresponding to a yield of 86%.

EXAMPLE 6

The procedure described in Example 1 is followed. Instead of diethylamine, 142 parts by weight of pyrrolidine are employed. 280 parts by weight of 1-pyrrolidinopent-2-yn-4-ol are obtained, corresponding to a yield of 91%.

EXAMPLE 7

255 parts by weight of 55% strength aqueous butynol, 250 parts by weight of 30% strength aqueous formaldehyde, 161 parts by weight of diethylamine, 2 parts by weight of copper sulfate, 2 parts by weight of iodine and 50 parts by weight of water are mixed with 115 parts by weight of concentrated sulfuric acid and then brought to pH 4.5 with sulfuric acid. The mixture is then heated for 5 hours at 95° C., cooled, mixed with 230 parts by weight of aqueous ammonia and extracted with 400 parts by weight of toluene. After distillation, 278 parts by weight of 1-diethylaminopent-2-yn-4-ol are obtained, corresponding to a yield of 89.5%.

We claim:

1. A process for the manufacture of an N-disubstituted 1-aminoalk-2-yn-4-ol by reaction of an optionally 3-mono- or di-substituted 3-hydroxypropyne with formaldehyde and an aliphatic secondary amine in aqueous acid solution in the presence of a copper compound, in accordance with the Mannich reaction, wherein the reaction is carried out in the presence of a bromide or iodide which is soluble in the reaction mixture, or in the presence of iodine.

2. A process for the manufacture of a 1-disubstituted aminoalk-2-yn-4-ol of the formula (I)

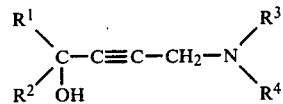

where $R^1$ is hydrogen or an aliphatic hydrocarbon radical and $R^2$ is hydrogen or an aliphatic or aromatic hydrocarbon radical, or $R^1$ and $R^2$ together with the carbon atom to which they are attached form a cycloaliphatic hydrocarbon radical, and $R^3$ and $R^4$ are each an aliphatic hydrocarbon radical, by reacting an alkynol of the formula

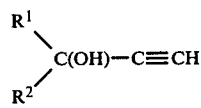

with formaldehyde and a secondary amine of the formula $R^3R^4NH$ in acid solution in the presence of a copper compound, in accordance with the Mannich reaction, wherein the reaction is carried out in the presence of a bromide or iodide which is soluble in the reaction mixture, or in the presence of iodine.

3. A process as claimed in claim 1, carried out in the presence of an alkali metal bromide or iodide.

4. A process as claimed in claim 1, carried out at a pH of 2 to 7 in the presence of a mineral acid.

5. A process as claimed in claim 1, wherein the copper compound is a copper(II) salt soluble in the reaction mixture.

6. A process as claimed in claim 4, carried out using copper (II) chloride, nitrate, acetate or sulfate as the copper compound.

7. A process as claimed in claim 1, carried out at 85° to 95° C.

* * * * *